United States Patent [19]

Buese et al.

[11] Patent Number: 4,800,872
[45] Date of Patent: Jan. 31, 1989

[54] RAVEL-FREE ORTHOPAEDIC CASTING TAPES

[75] Inventors: George J. Buese, East Brunswick; Hee K. Yoon, North Brunswick, both of N.J.

[73] Assignee: Johnson & Johnson Orthopaedics, Inc., New Brunswick, N.J.

[21] Appl. No.: 5,491

[22] Filed: Jan. 20, 1987

[51] Int. Cl.⁴ ............................................. A61F 5/04
[52] U.S. Cl. ................................ 128/90; 128/89 R;
    427/407.3; 427/434.2; 428/193; 428/425.6;
    428/913
[58] Field of Search ............... 128/89 R, 90, 156, 169;
    156/88; 427/407.3, 434.2; 428/193, 194, 425.6,
    913

[56] References Cited

U.S. PATENT DOCUMENTS

| | | | |
|---|---|---|---|
| 2,659,958 | 11/1953 | Johnson | 156/88 |
| 3,486,968 | 12/1969 | Mater | 128/156 |
| 3,630,194 | 12/1971 | Boardman | 128/90 |
| 3,881,473 | 5/1975 | Corvi et al. | 128/156 |
| 4,148,482 | 4/1979 | Harwell, Jr. et al. | 273/67 A |
| 4,320,634 | 3/1982 | Hashimoto et al. | 66/202 |
| 4,372,998 | 2/1983 | Shimada | 66/202 |
| 4,427,726 | 1/1984 | Wolfrum | 428/194 |
| 4,619,854 | 12/1986 | Penttinen | 427/407.3 |
| 4,667,661 | 5/1987 | Scholz et al. | 128/90 |
| 4,668,563 | 5/1987 | Buese et al. | 428/254 |

FOREIGN PATENT DOCUMENTS 1082878  5/1954  Austria ........................... 427/407.3

Primary Examiner—Richard J. Apley
Assistant Examiner—Paul B. Prebilic
Attorney, Agent, or Firm—Michael Q. Tatlow

[57] ABSTRACT

The casting tape substrate of the present invention is coated with a very soft, low modulus binder which is compatible with the polyurethane prepolymer or other curable resin which will be subsequently coated onto the substrate to form the casting tape. The binder prevents the cut ends of the substrate from unraveling. The binder may be applied in a pattern or continuously to the entire length of the substrate or may be applied at spaced zones where the knitted substrate will be cut to form a particular length of casting tape.

7 Claims, 3 Drawing Sheets

RAVEL-FREE ORTHOPAEDIC CASTING TAPES

FIELD OF THE INVENTION

The present invention relates to improved orthopaedic casting bandages made with knitted substrates containing fiberglass which are treated to prevent the raveling of the ends of the knitted fabric substrate.

BACKGROUND OF THE INVENTION

Plaster of paris casts to immobilize body members or limbs after fractures or breaks have been largely supplemented by synthetic casting tapes and bandages which employ polymeric materials in place of plaster of Paris. Polyurethane prepolymers, capable of being cured when reacted with water, have found wide use as replacement for plaster of Paris. The polyurethane prepolymers are coated on a fabric substrate to make the casting tape. The fabric substrate used in the synthetic casting materials has become to a large extent a fiberglass material. The fiberglass materials offer advantages in terms of strength of the finished cast and various constructions of fiberglass fabrics have been used as substrates for synthetic casting tapes. For the most part these fiberglass substrates have been Raschel knit fabrics. U.S. Pat. Nos. 3,686,725; 3,787,272 and 3,882,857 disclose specific fiberglass materials or the treatment of fiberglass materials to produce fiberglass substrates particularly suitable for use in orthopaedic casting tapes and bandages. U.S. Pat. No. 4,323,062 also disclose the cast substrate made from a combination of glass fibers and a second fiber such as cotton, flax, rayon, wool, acrylic, resin, nylon, or polyester.

Although fiberglass casting tapes have found extensive use in orthopaedic casting, one of the problems with fiberglass casting tapes is the tendency of the knitted fiberglass cast substrates to unravel on at least one end of the casting tape. As the tape is applied to the patient, there is one end of the tape which has a tendency to unravel and the unraveling causes the ends of the fiberglass substrate to become free and extend away from fabric substrate. As these free ends are coated with a prepolymer composition, they become stiff as the prepolymer cures and are like wire in their consistency. These free ends may be very uncomfortable for a patient if the wire-like end protrudes into the skin of the patient. The excessive raveling may also generate a considerable amount of loose strands in the casting tape which become unsightly and makes the casting tape difficult to apply. The unraveled end is not readily cut off from the bandage because of the nature of the prepolymer. The prepolymer is very sticky and attempting to cut the prepolymer coated substrate before curing is difficult. If the substrate contains only fiberglass it is possible to control the raveling problem to some extent by the use of high temperature heat treatment steps after the substrate is manufactured. However, the heat treatment does reduce the softness of the fabric and adversely alters the conformability of the casting tape. The raveling problem is particularly significant with highly conformable fiberglass substrates which contain elastic yarns. Fiberglass substrates containing elastic yarns, such as the substrate disclosed in co-pending application Ser. No. 873,648, filed June 12, 1986 now U.S. Pat. No. 4,668,583 cannot be heat treated because of the presence of the rubber or extensible filament in the substrate. The heat treatment would degrade the elastic yarn and the fabric would lose much of its elasticity.

SUMMARY OF THE PRESENT INVENTION

The present invention provides a method of treating substrates for orthopaedic casting tapes which prevents the raveling problem of untreated prior art fiberglass casting tapes. The casting tapes of the present invention are the standard Raschel knitted fiberglass substrates which may or may not contain elastic fiber in the substrate. The casting tape substrate of the present invention is coated with a very soft, low modulus binder which is compatible with the polyurethane prepolymer or other curable resin which will be subsequently coated onto the substrate to form the casting tape. The binder prevents the cut ends of the substrate from unraveling. The binder may be applied in a pattern or continuously to the entire length of the substrate or may be applied at spaced zones where the knitted substrate will be cut to form a particular length of casting tape.

DETAILED DESCRIPTION OF THE INVENTION

The casting tapes of the present invention are made by coating a reactive hardenable resin on a fiberglass substrate. The reactive hardenable resin may be any of the resins that have previously been disclosed for use in orthopedic bandages or casting tapes and which are cured by contacting the bandage with water or a solution containing a catalyst or curing agent for the resin. For example, epoxy resins are disclosed in U.S. Pat. No. 3,932,526; difunctional acrylates and methacrylates are disclosed in U.S. Pat. No. 3,908,644; diacetone acrylamine polymers are disclosed in U.S. Pat. No. 3,630,194 and polyurethane polymers are disclosed in U.S. Pat. Nos. 4,376,348 and 4,411,262. The preferred resins are polyurethanes. The polyurethanes are employed as prepolymers coated or impregnated on a fabric substrate to form the casting tape and then packaged in a moisture impervious packaging material until the casting tapes are used. The casting tapes are activated by immersing the tape into water which causes the prepolymer to cure. The casting tape is applied to the patient before the prepolymer is fully cured.

Figure 6:
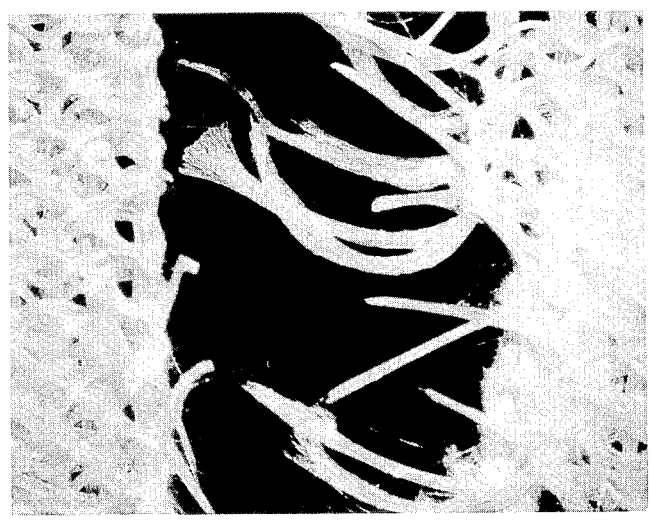
FIG. 6 is a photograph of a cut end of an uncoated substrate at the same magnification as FIG. 5

The fiberglass substrates are usually Raschel knit fabrics made on Raschel knitting machines employing two, three or four guidebars in making the knitted fabric. The Raschel knit fabrics have a tendency to unravel at one end of a piece of fabric cut from a length of the fabric. This ravel end is the end of the knitted fabric which is the trailing end of the fabric in relation to the knitting sequence. That is, the first portion of the fabric that is knitted will not tend to unravel because the knitted loops will lock the fibers together. In the trailing end of the fabric, if the fabric is cut, the loops tend to be cut and the fabric tends to come apart at that end as illustrated in FIG. 6. Although there can be some unraveling at the leading edge of the fabric, the degree of unraveling is relatively minor compared to the raveling at the trailing end of the fabric. The ravel problem is compounded when the fabric is made with elastomeric yarns combined with fiberglass yarns. As previously indicated, when the fabric is all fiberglass, it is possible to substantially overcome the ravel problem by heat treating the fabric at elevated temperatures. However, when elastomeric yarns are employed to produce highly conformable casting tapes, the heat treating step cannot be used because it will usually completely degrade the elastomeric yarns thus defeating their purpose. It has been found that it is possible to eliminate the ravel problem by coating the knitted fabrics with a soft binder material which is compatible with the polyurethane prepolymer. The binder should be capable of being applied to the fabric as a thin easily stretchable coating to bond the yarns in the fabric together to overcome the ravel. The binder should not markedly adversely affect the conformability of the fabric nor alter the open structure of the fabric. The binder also should not markedly affect the stability or shelf life of the prepolymer or diminish the crush strength of the finished cast. The low modulus binders that have been found to be useful for the present invention include binders made with acrylic resins and polyurethane resins, ethyl vinyl acetate polymers, ethylene propylene polymers, ethylene propylene diene polymers, butyl polymers, natural and synthetic rubber and polyester resins. The binders may be aqueous emulsions or solvent base solutions or dispersions at solid concentrations of from about 1 to 20 percent. The aqueous emulsions are preferred as they are more readily handled without extensive plant modifications which may be necessary to dry solvent based binder systems. The binders may also be hot melt materials. The binder should provide the following parameters to the coated substrate;

(a) The binder should prevent the casting tape from ravelling during the application of the casting tape to the patient. The binder coated substrate should inhibit the ravel so that not more than a few strands of relatively short length, approximately a ¼ to ⅜ of an inch are evident on either end of the casting tape.

(b) The binder should not give a harsh feel to the ends of the casting tape. Preferably, the binder on the tape will not be evident to the user of the tape. If the casting tape is harsh or stiff it will be difficult to adhere the tape to the underlying layers of tape previously applied to the patient. The adherence or lamination of overlapping layers of the casting tape to each other is necessary to obtain a strong cast with a smooth exterior surface. In order to meet this requirement, the coated substrate must have a "soft hand". The softness of the binder can be determined by a number of tests. The simplest method is using the Shore A or Type A durometer hardness. The Type A hardness of a sample of the binder should be 50 or below, and preferably between 15 and 50 and most preferably between 20 and 40 in order to give the requisite "hand" to the coated substrate. The Type A hardness of the binder is determined by placing a small sample of the binder, i.e., 3 to 6 grams, in a shallow flat bottom weighing dish and drying the binder by air drying or heating at a low temperature until dry. Additional amounts of the binder are added to the dish and dried until the layer of binder is about one/quarter inch thick. The hardness is determined directly on the dried sample according to the test method set forth as ASTM D2240. Another way in which the hardness can be characterized is by the temperature at which the torsional modulus of an air dried film of the binder is 300 Kg/cm$^2$. This value is referred to as the T 300 value. For the binders of the present invention, the T 300 value should be 0° C. or less, and preferably −20° C. or less.

(c) In addition to the physical attributes mentioned above, the coating should, preferably, not give any perceptive color to the finished cast and the coating material should not cause premature setting or gelling of the casting tape when the tape is in the package. The reactivity of the binder can readily be determined by coating the desired level of binder on a fiberglass substrate; applying the polyurethane prepolymer or other reactive resin to the coated substrate to make a casting tape; packaging the casting tape in a moisture impervious package; and storing the packaged tape in an oven at 70° C. until the casting tape hardens or cures in the package. If the tape does not harden within 25 days, the binder can be considered to be nonreactive with the polyurethane prepolymer or other resin used in making the casting tape. Typical of the binders that may be used are acrylic emulsions latices of that are commercially available from Valchem Chemical Co. under tradenames VALBOND 6002 and VALBOND 6004; a polyurethane latex available from WITCO Corporation under the tradename WITCOBOND W-170; a latex of a copolymer of butyl acrylate and ethyl acrylate with a small amount of acrylamide functionality available from Rohm and Haas as RHOPLEX TR-934; an ethylene propylene rubber latex available from Burke Palmason Chemical Co. under the tradename EP603A and a butyl rubber latex available from Burke Palmason under the tradename BL-100. There are numerous other binders which are useful in the practice of the present invention and which may be selected according to the criteria mentioned above.

These binders are applied to the substrate at very low coating levels between approximately 3 grams per sq. meter to approximately 90 grams per square meter based on the dry weight of the binder. These low coating levels are effective to eliminate the ravel problem in the fiberglass fabrics. Generally, the binder should be applied in the lowest amount necessary to prevent the ravel of the fabric substrate. Very soft binders may be applied at higher coating levels than harder binders. The preferable level of binder added is between 15 and 40 grams per square meter of fabric substrate. At the preferred level of binder addition, the binders with the requisite softness, i.e., Type A hardness below 50, will function to provide the desired properties.

The coating of the binder may be continuous over the entire length of the fabric substrate or the coating may be applied only in those portions of a continuous length of fabric substrate where the fabric will be cut to form the individual rolls of casting tape. The processes that may be used to apply the binder to the full length of the fabric include saturation coating, spraying, roller or rotogravure application or any of the processes used in the application of binders to nonwoven fabrics. Generally, the casting tape rolls are between 3 and 5 yards in length. It is possible to zone coat the fiberglass substrate so that the binder is applied only in that area where the substrate will be cut to the length of a roll of casting tape. The zone coating is applied to the full width of the substrate for a length of between 4 and 6 inches of the fabric every 3 to 5 yards. If desirable, it is also possible to incorporate into the binder a dye or other indicator so that the cutting machine can be indexed to the presence of the binder and the cutting can be done when the coated portion of the fabric reaches the cutting station in the equipment. It is also possible to coat the binder on the fabric in a pattern similar to the patterns used in applying binders to non-woven fabrics.

Figure 1:
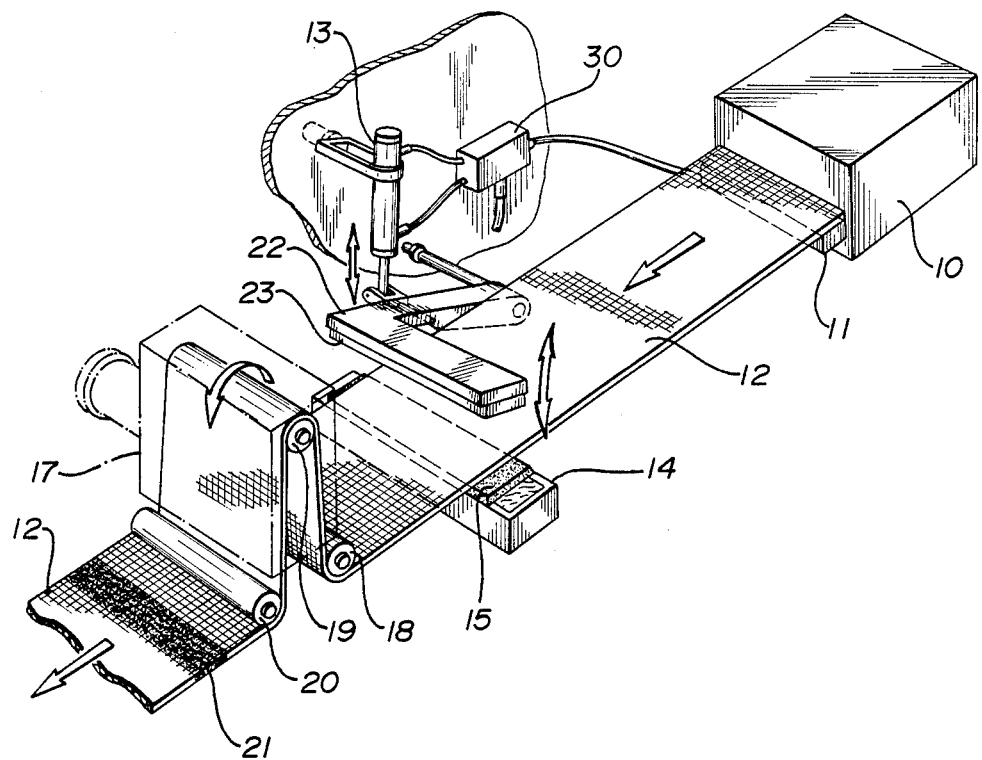
FIG. 1 is an isometric view of an apparatus to make the substrate of the present invention.
Figure 2:
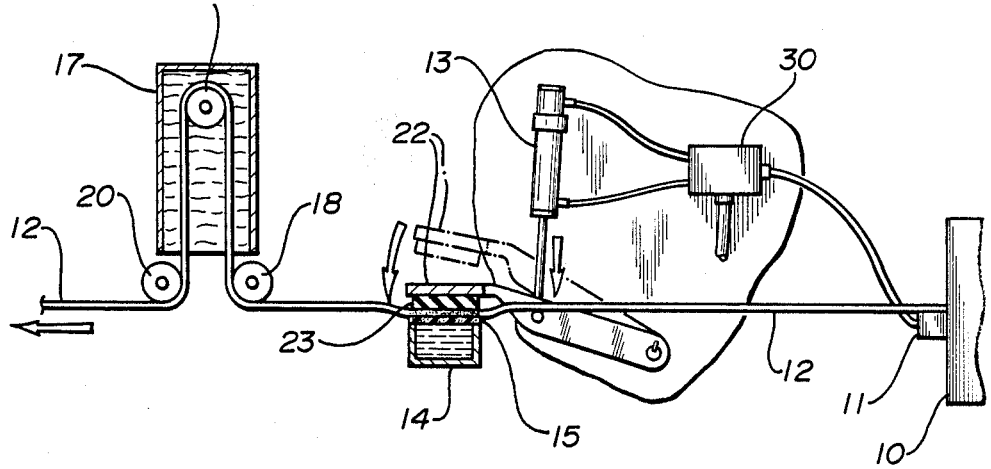
FIG. 2 is a side view of the apparatus of FIG. 1.

FIG. 1 and 2 illustrate one embodiment of a machine that can be employed to apply the binder to selected portions of the substrate. Numeral 10 indicates a Raschel knitting machine which produces the substrate. There may be a course counter 11 at the end of the knitting machine which counts the courses knitted, and therefore the length of the fabric. The course counter is connected to a controller 30 which controls a piston 13. The piston 13 can move an arm 22 up or down. The arm 22 has a pad 23 on its lower surface. There is a container 14 filled with the binder material. An absorbent pad 15 is in contact with the binder material in the container. When the arm 22 is moved downward the pad 23 contacts the fabric 12 and moves the fabric into contact with the binder material held on the pad 15. When a predetermined number of courses have been knitted by the machine, the piston 13 is activated and moves the arm 22 downward. The pad 23 contacts the fabric 12 and moves the fabric into contact with the binder material held on the pad 15. The arm 22 is then immediately lifted. It should be understood that the speed of the knitting machine is quite slow and that the momentary interruption of the movement of the fabric while the pads 15 and 23 are squeezed together would not adversely affect the fabric leaving the knitting machine. After the binder has been applied, the fabric is directed into a dryer which is shown schematically at 17 to evaporate the water or other solvent and dry the fabric. The fabric moves around rollers 18, 19 and 20 in the dryer. The coated segment of the fabric, is shown as 21 in FIG. 1.

Figure 3:
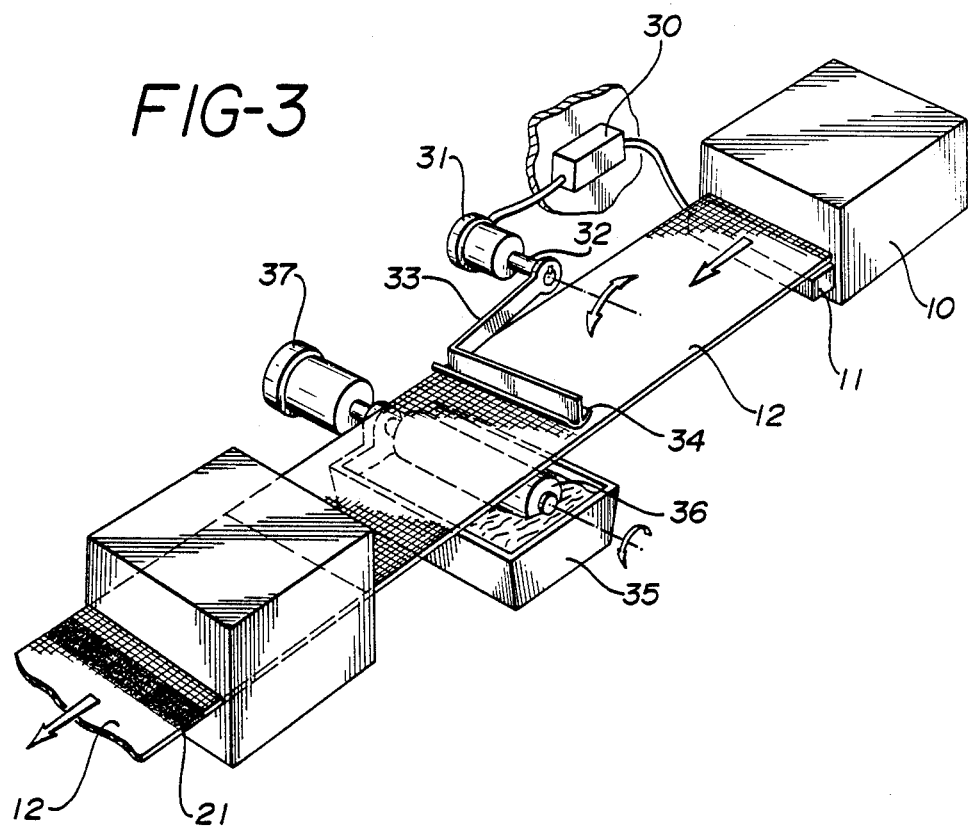
FIG. 3 is an isometric view of a second embodiment of an apparatus to make the substrate of the present invention.
Figure 4:
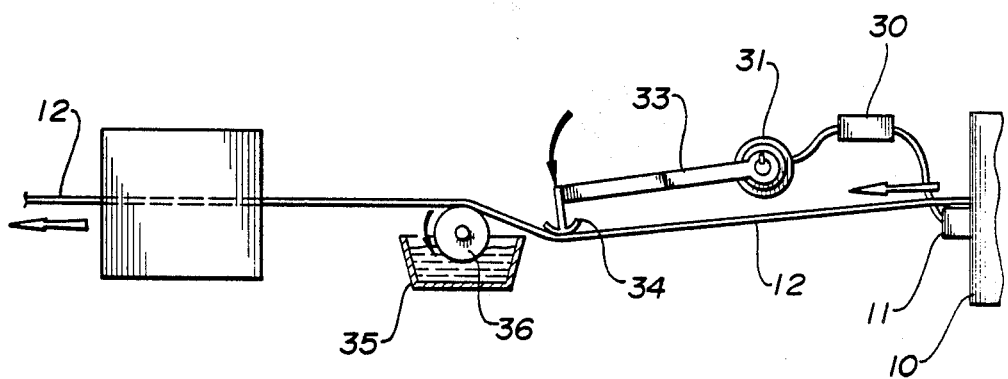
FIG. 4 is a side view of the apparatus of FIG. 3.

The apparatus shown in FIGS. 3 and 4 is another and the preferred embodiment of an apparatus that is used to coat the fabric. The fabric is produced on a Raschel knitting machine 10 and its length can be determined by a course counter 11 which is connected to a controller 30. The controller is connected to a servomotor 31 having an arm 33 attached to the shaft 32 of the servomotor. There is an arcuate plate 34 attached to the arm and capable of moving downward to contact the fabric when the motor 31 is activated. There is a tank 35 containing the binder below the fabric. There is a roller 36 rotated at slow speed by a motor 37 in contact with the binder in the tank 35. When the course counter 11 indicates that a predetermined number of courses (and therefore length of fabrics) have been knitted, a signal is sent to the controller 30. The controller activates the servomotor 31, which turns the shaft 32 and forces the plate 34 to deflect the fabric so that the fabric contacts the roller 36 for a predetermined period of time. The controller then reverses the servomotor 31 and the plate is lifted from contact with the fabric. The contact of the fabric by the roller 36 transfers the binder to the fabric in a 4 to 6 inch band across the width of the fabric.

Figure 5:
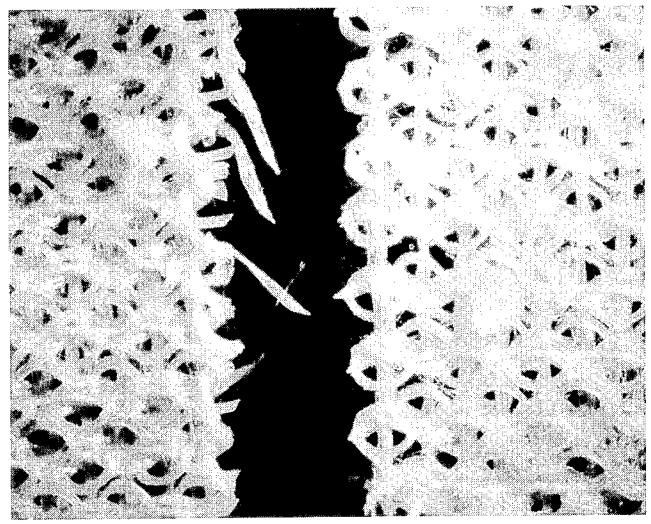
FIG. 5 is a photograph of a cut end of the coated substrate of the present invention at a magnification of 5X.

FIGS. 5 and 6 illustrate a substrate of the present invention which has been coated, FIG. 5, and a similar substrate which has not been coated, FIG. 6. Both fabrics were cut and the cut edges placed next to each other. The ravel end of the fabric is that on the left side of FIG. 5 and right side of FIG. 6. It is quite clear that the coated fabric does not ravel to any great extent.

The water reactive hardenable resin is applied to the binder coated substrate by any of the procedures usually employed in the manufacture of casting tapes. After the resin is applied, the substrate is cut to predetermined or definitive lengths and rolled to form an individual casting tape. The tape is packaged in a moisture impervious package so that it will not be prematurely cured from ambient moisture.

EXAMPLE I

An acrylic acid polymer resin binder sold under the name of VALBOND 6004 was formulated into an 8% solid dispersion by mixing with water. The binder was applied to a roll of cold cleaned fiberglass fabric, which fabric has been used in a commercially available casting tape and which readily ravels, by passing the fabric through a trough containing the binder. The coating weight of the binder is about 20 grams per square meter. The excess binder was removed from the fabric by passing the fabric between the rubber rollers on an Atlas laboratory wringer with a pressure of 100 pounds on the rollers. The coated fabric was then air dried for approximately 6 hours. The fabric was then wrapped on a core and dried for three hours at 100° C. under high vacuum. The fabric was then coated with a polyurethane prepolymer at an add-on level of 43% by weight in a dry box. Casting tapes were prepared from the coated fabric and sealed in commercial metal-foil packaging. The packages were placed in a 70° C. oven to age. The casting tapes were evaluated after 29 days in the oven and they were found to be soft and not cured. They had only a few strands at the ravel end of the tape. The casting tapes were dipped in water and wrapped to form casts. The casts had good color and appearance and good lamination between layers. The oven aging of the casting tapes at 70° C. for 29 days is equivalent to a shelf life of about 4 years at 70° F.

EXAMPLE II

The procedure set forth in Example I was repeated using different binder systems. The results are shown below:

| Binder (Tradename) | Binder coating weight gms/sq M | Type A Hardness | Shelf life at 70° C. |
|---|---|---|---|
| Acrylic Acid Polymer (VALBOND 6004) | 21.39 | 28 to 32 | 34 days |
| Acrylic Acid-Ethyl Acrylate (RHOPHEX TR-934) | 21.7 | 22 to 30 | 34 days |
| Ethylene Propylene Rubber (EP 603A) | 21.39 | 28 to 38 | 29 days |
| Butyl Rubber Latex (BL-100) | 19.07 | 20 to 24 | 29 days |

EXAMPLE III

A 1.25 percent solid, dispersion was prepared by adding water to a WITCOBOND W-170 polyurethane dispersion. This dispersion was overall coated on a 4 inch wide enzyme cleaned knitted fiberglass fabric, similar to that employed in Example I. The coating process was the same process as in Example I. The coating weight of the binder was about 3.1 grams per square meter. The coated fabric was dried and coated with the polyurethane prepolymer used in a commercial casting tape. The prepolymer was added at approximately 37% to 39% by weight add-on. The prepolymer coated fabric was made into 4-yard long casting tapes that were sealed in commercial metal foil packages. The casting tapes were aged for 2 years at room temperature and were found soft and stretchable and had good nonravel properties. Other samples of the same casting tapes were evaluated and had excellent crush strength, 128 pounds for a 5-wrap cast after curing at 24 hours, and were very conformable and comparable to commercially available fiberglass polyurethane casting tapes.

EXAMPLE IV

A knitted fiberglass fabric which contained a 95 gauge natural rubber yarn of the type described in our copending application, Ser. No. 873,648, filed June 12, 1986 was coated employing the process depicted in FIGS. 3 and 4 of the present application. The fabric was coated with the Rohm & Haas acrylic latex binder designated RHOPLEX TR-934 and then dried. The fabric binder had a type A hardness in the range of 22 to 30. The binder contained a few drops, less than 1/10 of one percent, of Leucophor BSB, an ultraviolet indicator, which fluoresces when subjected to ultra violet light and indicates the area where the fabric should be cut to form a length of casting tape. The coating level was approximately 22 grams per square meter. The binder-coated areas, which measured about 6 inches long by the full 3 inch width of the fabric, were separated from each other by about 3.2 yards. The fabric was dried, and the roll of substrate was overcoated with the prepolymer described in Example I at a coating level of 41% to 42%. Casting tapes were prepared from this coated roll by cutting the fabric at the midpoint of the binder-coated areas and were packaged in foil packages similar to those mentioned in the previous examples. The casting tapes were evaluated before and after aging at 70° C. The ends of the fabric were soft, flexible and exhibited very good nonravel properties. Casts made from these bandages had cast strengths, at 24 hours, of 82 pounds for 5 wraps of the 3-inch width cast tape prepared on a 2⅜ inch diameter spindle. This is comparable to commercially available cast bandages. Bandages which were evaluated after aging 13 days at 70° C., equivalent to about two years at 70° F., still performed satisfactorily indicating the bandages had good shelf life.

We claim:

1. A ravel resistant, orthopedic casting tape of the type comprising of knitted fiberglass substrate impregnated with a water reactive, hardenable, liquid resin, said substrate being coated, prior to the application of the liquid hardenable resin, with a soft, flexible binder to form a thin, stretchable coating to resist ravel of the fiberglass, said binder being essentially not reactive with the hardenable liquid resin and the binder having a type A hardness less than 50, and being applied to the substrate in an amount from 2.5 to 90 grams per square meter of coated area.

2. The casting tape of claim 1 in which the binder is applied only at the ends of a finite length of said casting tape.

3. The casting tape of claim 1 in which the binder has a Type A hardness between 15 and 50.

4. The casting tape of claim 2 in which the binder includes an indicator which fluoresces when subjected to ultraviolet light.

5. The casting tape of claim 1 in which the binder is an acrylic polymer.

6. The casting tape of claim 1 in which the binder is a polyurethane polymer.

7. The casting tape of claim 3 in which the binder has a Type A hardness between 20 and 40.

* * * * *